United States Patent
Machida et al.

(10) Patent No.: US 10,578,604 B2
(45) Date of Patent: Mar. 3, 2020

(54) ELECTRICAL CHARACTERISTIC MEASURING DEVICE

(71) Applicant: SONY CORPORATION, Tokyo (JP)

(72) Inventors: Kenzo Machida, Kanagawa (JP);
Marcaurele Brun, Tokyo (JP);
Yoshihito Hayashi, Chiba (JP)

(73) Assignee: SONY CORPORATION, Tokyo (JP)

( * ) Notice: Subject to any disclaimer, the term of this patent is extended or adjusted under 35 U.S.C. 154(b) by 66 days.

(21) Appl. No.: 15/509,091

(22) PCT Filed: Aug. 10, 2015

(86) PCT No.: PCT/JP2015/072603
§ 371 (c)(1),
(2) Date: Mar. 6, 2017

(87) PCT Pub. No.: WO2016/042944
PCT Pub. Date: Mar. 24, 2016

(65) Prior Publication Data
US 2017/0276662 A1    Sep. 28, 2017

(30) Foreign Application Priority Data

Sep. 19, 2014   (JP) .................................. 2014-191611

(51) Int. Cl.
  *G01N 33/49*     (2006.01)
  *G01N 27/02*     (2006.01)

(52) U.S. Cl.
  CPC .......... *G01N 33/49* (2013.01); *G01N 27/026* (2013.01); *G01N 33/491* (2013.01)

(58) Field of Classification Search
  CPC .......................... G01N 33/49; G01N 27/026
  See application file for complete search history.

(56) References Cited

U.S. PATENT DOCUMENTS

| | | | | |
|---|---|---|---|---|
| 4,547,735 A | * | 10/1985 | Kiesewetter | G01N 33/49 324/442 |
| 5,583,432 A | * | 12/1996 | Barnes | G01N 15/05 324/204 |
| 2009/0314066 A1 | * | 12/2009 | Nieuwenhuis | G01N 15/0656 73/61.71 |
| 2012/0265037 A1 | * | 10/2012 | Bohm | G01N 27/3274 600/309 |
| 2014/0330244 A1 | * | 11/2014 | Hyde | A61B 5/076 604/503 |

FOREIGN PATENT DOCUMENTS

| | | |
|---|---|---|
| JP | 59-147265 A | 8/1984 |
| JP | 07-280814 A | 10/1995 |

(Continued)

*Primary Examiner* — Akm Zakaria
(74) *Attorney, Agent, or Firm* — Chip Law Group

(57) ABSTRACT

To an electrical characteristic measuring device that further improves the accuracy of measurement of an electrical characteristic of a blood sample. Provided is an electrical characteristic measuring device including: a measuring unit configured to measure an electrical characteristic of a blood sample; and an alert generation unit configured to issue an alert signal when an erythrocyte sedimentation rate in the blood sample exceeds a prescribed standard during measurement of the blood sample.

7 Claims, 13 Drawing Sheets

(56) References Cited

FOREIGN PATENT DOCUMENTS

| | | |
|---|---|---|
| JP | 2007-107889 A | 4/2007 |
| JP | 2012-194087 A | 10/2012 |
| JP | 2014-115256 A | 6/2014 |
| WO | 2014/112227 A1 | 7/2014 |
| WO | 2014/141844 A1 | 9/2014 |

* cited by examiner

ELECTRICAL CHARACTERISTIC MEASURING DEVICE

CROSS REFERENCE TO RELATED APPLICATIONS

This application is a U.S. National Phase of International Patent Application No. PCT/JP2015/072603 filed on Aug. 10, 2015, which claims priority benefit of Japanese Patent Application No. JP 2013-191611 filed in the Japan Patent Office on Sep. 19, 2014. Each of the above-referenced applications is hereby incorporated herein by reference in its entirety.

TECHNICAL FIELD

The present technology relates to an electrical characteristic measuring device and a program. More specifically, the present technology relates to a technology that improves the accuracy in the measurement of an electrical characteristic of a blood sample.

BACKGROUND ART

There is known a method in which an electrical characteristic of a sample derived from blood is measured and thereby the sample is analyzed. However, in a sample containing a liquid component such as blood plasma and blood cell components such as red blood cells, there has been a case where, during the measurement of the sample, blood cell components sediment and the relative positions in the measurement container or the like change, and consequently accurate measurement of the electrical characteristic becomes difficult.

To address such a problem that blood cell components sediment, for example, Patent Literature 1 discloses "an electrical measuring container of liquid biological samples that includes at least a biological sample holding unit made of resin for storing a liquid biological sample and an electrically conductive unit fixed to the biological sample holding unit and in which the biological sample holding unit and the electrically conductive unit are integrally molded in a state where a part of the electrically conductive unit is embedded in the biological sample holding unit." In the electrical measuring container, an electrode unit provided in the electrically conductive unit may be placed on the upper side of the portion that forms the bottom surface during measurement, with a prescribed distance from this portion, for example; thereby, even when sedimentable components sediment in the biological sample, accurate measurement can be performed without influence on the measurement value up to part of the way.

CITATION LIST

Patent Literature

Patent Literature 1: JP 2014-115256A

DISCLOSURE OF INVENTION

Technical Problem

The electrical characteristic of a blood sample can be measured with high accuracy by the electrical measuring container described in Patent Literature 1 above. However, the rate of sedimentation of blood cell components may greatly vary depending on blood samples, and further improvement has been desired in order to measure the electrical characteristic of a blood sample with high accuracy.

Thus, a main object of the present disclosure is to provide an electrical characteristic measuring device that further improves the accuracy of measurement of an electrical characteristic of a blood sample.

Solution to Problem

In order to solve the above problem, the present disclosure provides an electrical characteristic measuring device including: a measuring unit configured to measure an electrical characteristic of a blood sample; and an alert generation unit configured to issue an alert signal when an erythrocyte sedimentation rate in the blood sample exceeds a prescribed standard during measurement of the blood sample.

The alert generation unit may assess whether the erythrocyte sedimentation rate exceeds a prescribed standard on the basis of an electrical characteristic obtained by measuring the blood sample.

The alert generation unit may use one or more permittivities at a specific frequency as the electrical characteristic.

The alert generation unit may use, as the permittivity, a permittivity measured at a specific time point after a start of measurement of the blood sample.

The alert generation unit may use, as the permittivity, a plurality of permittivities at mutually different frequencies and assesses whether the erythrocyte sedimentation rate exceeds a prescribed standard on the basis of a relationship between the plurality of permittivities.

The alert generation unit may assess whether the erythrocyte sedimentation rate exceeds a prescribed standard on the basis of a temporal change in the permittivity.

The alert generation unit may assess whether the erythrocyte sedimentation rate exceeds a prescribed standard on the basis of an increase or decrease in the permittivity per certain time.

The measuring unit may include at least a pair of electrodes in a position in contact with the blood sample.

The pair of electrodes may be arranged facing each other, and surfaces of the electrodes facing each other may be disposed along a direction in which red blood cells in the blood sample sediment.

The electrical characteristic measuring device may include a first alert presentation unit configured to present an alert during measurement of the blood sample on the basis of the alert signal.

The measuring unit may stop measurement of the blood sample on the basis of the alert signal.

The electrical characteristic measuring device may include a second alert presentation unit configured to present, for data obtained by measuring the electrical characteristic, presence or absence of the alert signal generated during measurement.

According to the present disclosure, there is also provided a program for causing a computer to execute: a measurement function of measuring an electrical characteristic of a blood sample; and an alert generation function of issuing an alert signal when an erythrocyte sedimentation rate in the blood sample exceeds a prescribed standard during measurement of the blood sample.

Advantageous Effects of Invention

According to the present disclosure, an electrical characteristic measuring device that further improves the accuracy of measurement of an electrical characteristic of a blood sample etc. are provided. The effect described herein is not necessarily limited, and may be any effect described in the present disclosure.

BRIEF DESCRIPTION OF DRAWINGS

FIG. 13A shows the real part, and FIG. 13B shows the imaginary part.

MODE(S) FOR CARRYING OUT THE INVENTION

Hereinbelow, preferred embodiments of the present disclosure are described. The embodiments described below show typical embodiments of the present disclosure, and the scope of the present disclosure should not be construed as being limited by them. The description is given in the following order.

1. First embodiment (configuration including first alert presentation unit)
2. Modification embodiment of first embodiment (configuration in which measuring unit stops measurement by means of alert signal)
3. Second embodiment (configuration including second alert presentation unit)

1. First Embodiment

Figure 1:
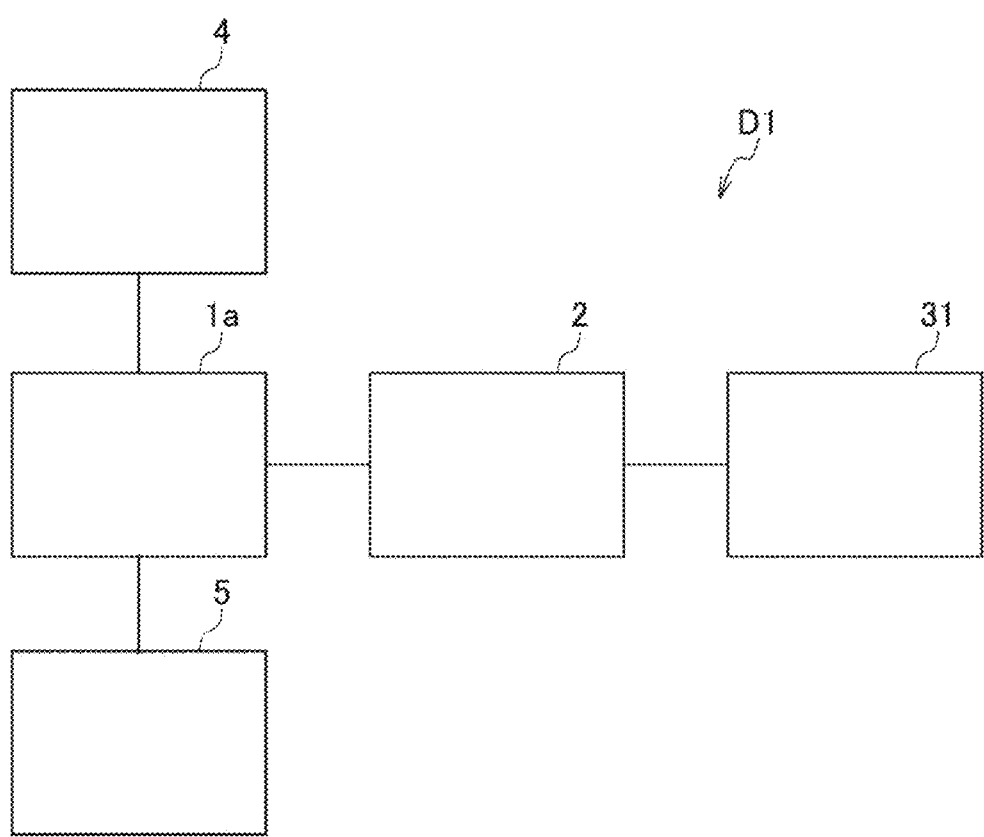
FIG. 1 is a schematic diagram showing the configuration of an electrical characteristic measuring device according to a first embodiment of the present disclosure.

An electrical characteristic measuring device according to a first embodiment of the present disclosure will now be described. FIG. 1 is a schematic diagram showing the configuration of an electrical characteristic measuring device of the embodiment. The electrical characteristic measuring device indicated by reference character D1 includes a measuring unit 1$a$ and an alert generation unit 2. The electrical characteristic measuring device D1 preferably includes a first alert presentation unit 31. Other than these, a display unit 4 and a memory unit 5 may be provided in the electrical characteristic measuring device D1. The configuration of each part of the electrical characteristic measuring device D1 will now be described in order.

<Measuring Unit>

In the electrical characteristic measuring device D1, the measuring unit 1$a$ at least measures an electrical characteristic of a blood sample. The value specifically measured as the electrical characteristic by the measuring unit 1$a$ may be selected in accordance with, for example, the objective of analyzing the blood sample, such as the analysis of blood coagulability, etc. as appropriate, and may be impedance, permittivity, or the like, for example. The configuration of the measuring unit 1$a$ may be freely designed to the extent that it is configured such that the electrical characteristic of the measurement objective can be measured for the blood sample. In the case where, for example, impedance or permittivity is measured as the electrical characteristic, an impedance analyzer, a network analyzer, or the like may be employed as the measuring unit 1$a$.

In the present disclosure, the "blood sample" may be a sample containing red blood cells and a liquid component such as blood plasma, and is not limited to the blood itself. A reagent may be added in a prescribed concentration to the blood sample in accordance with the objective of measuring the electrical characteristic, etc. Examples of the reagent include an anticoagulant, a drug for an anticoagulant, etc. Examples of these reagents include a calcium aqueous solution, various blood coagulation factors, various coagulation reagents, a heparin neutralizer, a fibrinolytic system inhibitor, a platelet inhibitor, a platelet activator, etc.

Figure 2:
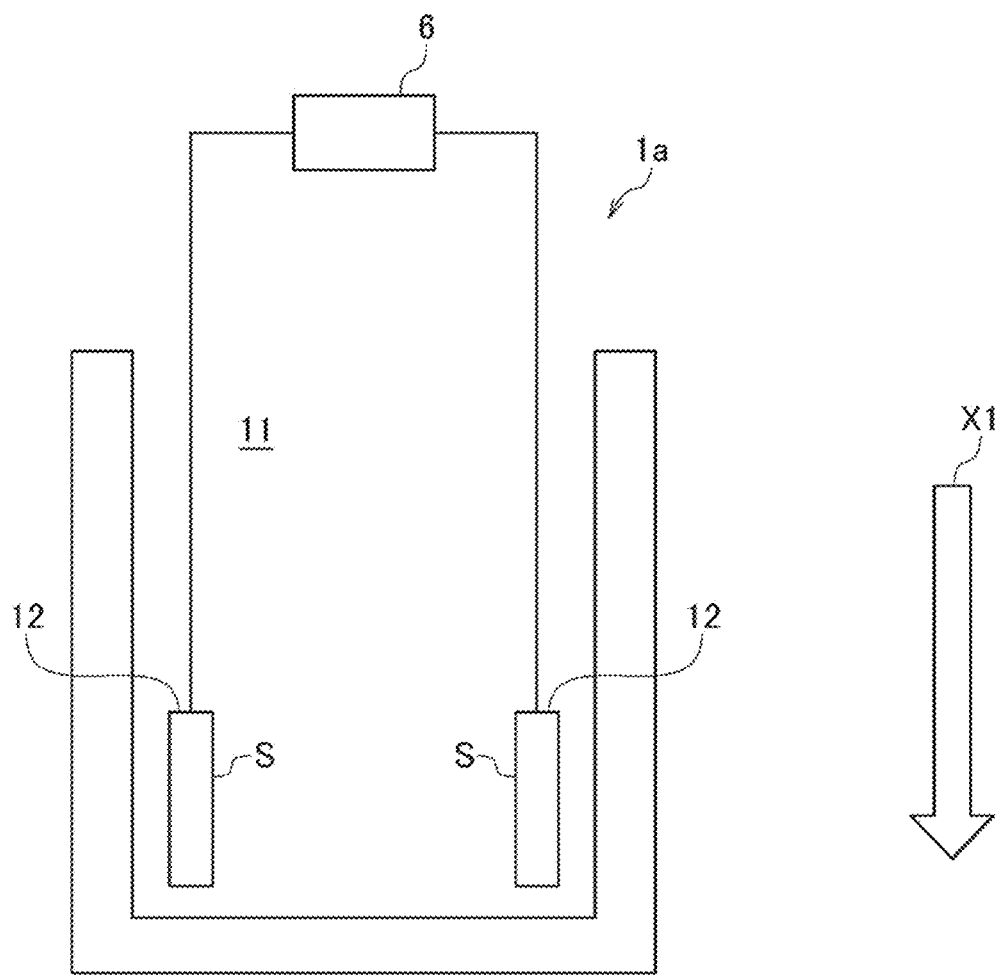
FIG. 2 is a schematic diagram showing an example of the sample storage space and the electrode pair provided in a measuring unit.

FIG. 2 schematically shows an example of the configuration of the measuring unit 1$a$. As shown in FIG. 2, a space in which a blood sample can be stored at least during the measurement of the blood sample (a sample storage space 11) is provided in the measuring unit 1$a$. The member that separates the sample storage space 11 and the outside may be selected from known materials as appropriate to the extent that it is an insulating material. Examples of the insulating material include a hydrophobic and insulating polymer, copolymer, blend polymer, and the like, such as polypropylene, polymethyl methacrylate, polystyrene, and polytetrafluoroethylene. The sample storage space 11 may be configured using a container so as to be detachable from the measuring unit 1$a$, for example. The measuring unit 1$a$ may be configured so as to be able to measure the electrical characteristic of one blood sample, or may be configured so as to be able to measure the electrical characteristics of a plurality of blood samples simultaneously.

The measuring unit 1a preferably includes at least a pair of electrodes 12 and 12 in a position in contact with the blood sample. A voltage may be applied between the pair of electrodes 12 and 12 by an application unit 6, and thereby the electrical characteristic of the blood sample can be measured, for example.

The material of the electrodes 12 and 12 may be selected from known materials as appropriate to the extent that it is an electrically conductive material having little influence on the blood sample. Examples of the material of the electrodes 12 and 12 include titanium, aluminum, stainless steel, platinum, gold, copper, graphite, and the like.

In the measuring unit 1a, the pair of electrodes 12 and 12 are preferably arranged facing each other. Further, the surfaces (facing surfaces) S and S of the electrodes 12 and 12 that face each other are preferably disposed along the direction in which red blood cells in the blood sample sediment (see arrow X1 of FIG. 2). Since the facing surfaces S and S of the electrodes 12 and 12 are formed along the direction of sedimentation of red blood cells, by adjusting the arrangement of the electrodes 12 and 12, the electrodes can be made less susceptible to the sedimentation of red blood cells occurring during the measurement of the blood sample. For example, the electrodes 12 and 12 may be formed in a lower portion of the sample storage space 11; thereby, the time until a blood plasma layer produced due to the progress of sedimentation of red blood cells reaches the electrodes 12 and 12 can be made longer, and the measurement of the electrical characteristic of the blood sample can be prevented from being influenced by the blood plasma layer for a longer period of time. On the other hand, in the case where the facing surfaces S and S of the electrodes are formed along a direction crossing the direction of sedimentation of red blood cells, one facing surface S placed in an upper portion of the sample storage space 11 forms the substantially uppermost surface of the blood sample, and the measurement of the electrical characteristic based on the sedimentation of red blood cells may be influenced earlier.

<Alert Generation Unit>

The alert generation unit 2 issues an alert signal when the erythrocyte sedimentation rate in a blood sample exceeds a prescribed standard during the measurement of the blood sample. The "erythrocyte sedimentation rate" is the rate at which red blood cells sediment through the blood plasma, and is called also "Sekichin" or "Ketchin" in Japanese.

In the present disclosure, the prescribed standard for the erythrocyte sedimentation rate may be determined on the basis of the erythrocyte sedimentation rate measured in a blood sample derived from an able-bodied person, for example. That is, "the erythrocyte sedimentation rate exceeds the prescribed standard" means that the sedimentation of red blood cells is faster than that of a blood sample derived from an able-bodied person. It is also possible to use, as the standard, the upper limit value of the erythrocyte sedimentation rate in a range in which the measurement of the electrical characteristic in the measuring unit 1a described above can be performed appropriately.

The configuration of the alert generation unit 2 is not particularly limited and may be freely designed to the extent that it is configured so as to be able to issue an alert signal when the erythrocyte sedimentation rate exceeds a prescribed standard. For example, the alert generation unit 2 may be configured using a general-purpose computer including a memory, a CPU, etc.

When the alert generation unit 2 assesses whether the erythrocyte sedimentation rate exceeds a prescribed standard on the basis of the electrical characteristic described later, the alert generation unit 2 may, after the start of measurement of the electrical characteristic by the measuring unit 1a, continuously acquire measurement values of the electrical characteristic etc., for example. In the case where, for example, the alert generation unit 2 uses the measurement result at a prescribed time point after the start of measurement in order to assess the erythrocyte sedimentation rate, the alert generation unit 2 may acquire only the measurement value of the electrical characteristic at the prescribed time point after the start of measurement.

<First Alert Presentation Unit>

The first alert presentation unit 31 presents an alert during the measurement of a blood sample on the basis of an alert signal. The configuration of the first alert presentation unit 31 is not particularly limited and may be freely designed to the extent that it has the function of presenting an alert to the user on the basis of an alert signal. For example, a display, a printer, a loudspeaker, a lighting device, etc. may be employed as the first alert presentation unit 31. Also a device having a communication function for transmitting, to a mobile device such as a mobile phone or a smartphone, an e-mail or the like for giving information that an alert signal is generated may be employed for the first alert presentation unit 31, for example. Further, the devices described above may be combined in the first alert presentation unit 31.

"The presentation of an alert" can be made by displaying a character, a figure, etc. on a display, or printing out them with a printer, for example. Other than these, an alert may be presented to the user by turning on or turning on and off a lighting device or the like. In addition, to inform the user of an alert, an alert sound or the like may be produced as "the presentation of an alert." Also the transmission of an e-mail or the like to a mobile device such as a mobile phone or a smartphone may be used as an alert to the user. The methods described above by which the user can recognize the generation of an alert signal may be combined in "the presentation of an alert."

<Display Unit>

The display unit 4 is a configuration for displaying the electrical characteristic measured by the measuring unit 1a etc. The configuration of the display unit 4 is not particularly limited to the extent that it can display the measurement result of the electrical characteristic etc. For example, a display, a printer, etc. may be employed for the display unit 4.

<Memory Unit>

The memory unit 5 is a configuration for storing the measurement result of the electrical characteristic measured by the measuring unit 1a etc. Also the operating program of the electrical characteristic measuring device D1 etc. may be stored. The memory unit 5 may be selected from known memory media in accordance with the structure of the electrical characteristic measuring device D1 etc., as appropriate. Examples of the memory medium include a hard disk drive, a flush memory, a solid state drive (SSD), etc.

In the electrical characteristic measuring device D1, a control unit for controlling the entire electrical characteristic measuring device D1, an input unit to which the user inputs the operating program of the electrical characteristic measuring device D1 etc., and other units may be provided other than the above (the the control unit and the input unit are not shown in FIG. 1). In the case where a general-purpose computer including a memory, a CPU, etc. is employed for the control unit for controlling the entire electrical characteristic measuring device D1, the alert generation unit 2 and the control unit described above may be configured using one general-purpose computer.

<Operation>

Figure 3A:
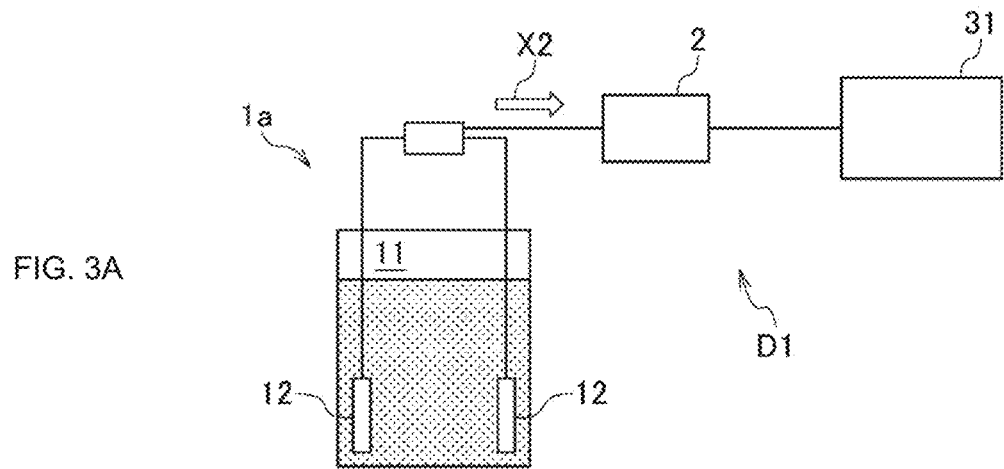
FIGS. 3A to 3C are schematic diagrams showing the operation of the electrical characteristic measuring device according to the first embodiment.
Figure 3B:
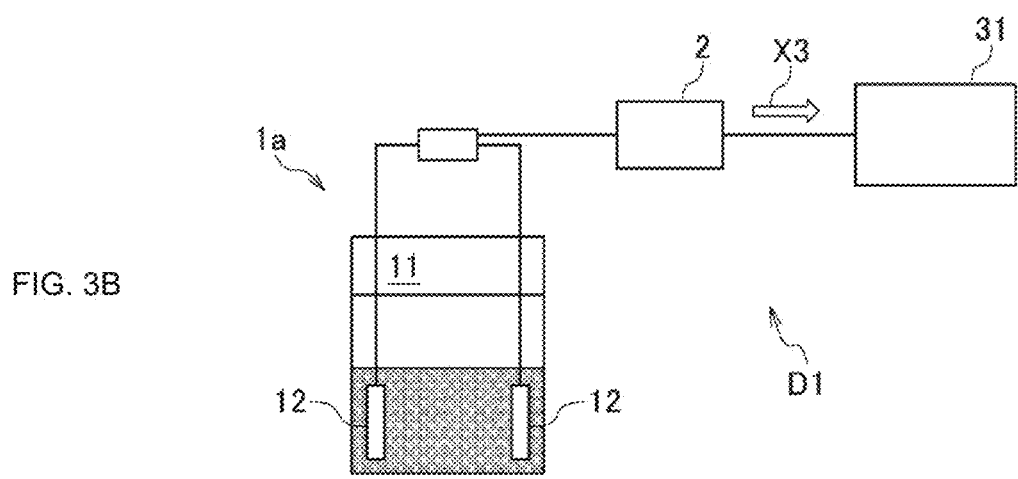
Figure 3C:
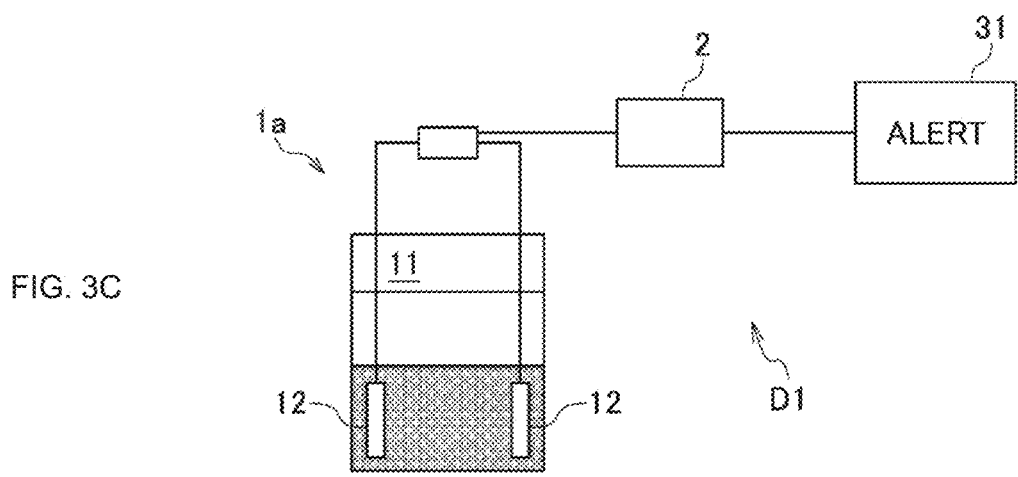

The operation of the measuring unit 1a, the alert generation unit 2, and the first alert presentation unit 31 in the electrical characteristic measuring device D1 described above will now be described. FIGS. 3A, 3B and 3C are schematic diagrams showing the operation of the electrical characteristic measuring device D1.

In the electrical characteristic measuring device D1, first, the measurement of the electrical characteristic of a blood sample by the measuring unit 1a is started (see FIG. 3A). In the case where, as described later, the alert generation unit 2 compares the erythrocyte sedimentation rate and a prescribed standard on the basis of the electrical characteristic of the blood sample, the alert generation unit 2 may acquire the result of measurement of the electrical characteristic by the measuring unit 1a continuously, alternatively at regular intervals, or alternatively at a prescribed time point after the start of measurement (see arrow X2 of FIG. 3A).

After the start of measurement of the electrical characteristic in the blood sample, when the erythrocyte sedimentation rate exceeds a prescribed standard, the alert generation unit 2 issues an alert signal (see arrow X3 of FIG. 3B). Since the electrical characteristic measuring device D1 according to the embodiment includes the first alert presentation unit 31, the first alert presentation unit 31 presents an alert on the basis of a signal issued from the alert generation unit 2 (see FIG. 3C).

In the case where, for example, a plurality of measuring units 1a are provided in the electrical characteristic measuring device D1 and a plurality of blood samples are measured simultaneously, the number, the sample name, the ID, or the like of a blood sample in which the erythrocyte sedimentation rate exceeds a prescribed standard may be presented along with an alert. The period of time during which an alert is presented is not particularly limited. For example, the presentation of an alert may continue for a prescribed period of time, or may continue until the measurement of the blood sample finishes.

The assessment by the alert generation unit 2 of whether the erythrocyte sedimentation rate exceeds the prescribed standard may be performed on the basis of any index by which the erythrocyte sedimentation rate can be estimated. It is preferable for the alert generation unit 2 to assess whether the erythrocyte sedimentation rate exceeds the prescribed standard on the basis of the electrical characteristic obtained by measuring the blood sample. By using the electrical characteristic measured by the measuring unit 1a for the assessment, a configuration for measuring the erythrocyte sedimentation rate does not need to be provided separately in the electrical characteristic measuring device D1, and the size of the device can be kept small.

The alert generation unit 2 may use, as the electrical characteristic described above, one or more permittivities at a specific frequency. The frequency may be set in accordance with the configuration of the measuring unit 1a, the characteristic of the blood sample, the objective of analyzing the blood sample, etc. as appropriate. The permittivity mentioned above may be what is measured as a dielectric spectrum, in accordance with the configuration of the measuring unit 1a etc.

The assessment of the erythrocyte sedimentation rate based on the electrical characteristic in the alert generation unit 2 will now be described using the case of using permittivity as an example. The permittivity used for the assessment of the erythrocyte sedimentation rate may be a permittivity normalized by a value measured at a prescribed time point after the start of measurement of the electrical characteristic by the measuring unit 1a or the like, for example.

For example, the alert generation unit 2 may use, as the permittivity mentioned above, the permittivity measured at a specific time point after the start of measurement of the blood sample. In this case, the alert generation unit 2 may compare the permittivity measured at the specific time point and a prescribed threshold, and may thereby assess whether the erythrocyte sedimentation rate in the blood sample exceeds the prescribed standard.

For the threshold for use by the alert generation unit 2, for example, the electrical characteristic of a blood sample in which the erythrocyte sedimentation rate is found to be within the range of normal values may be measured in advance, and a specific value may be determined from the obtained measurement result. Other than this, the electrical characteristic may be measured using a blood sample that is found to be able to be appropriately measured in the measuring unit 1a, and a specific value may be determined from the obtained measurement result.

The alert generation unit 2 may use, as the permittivity mentioned above, a plurality of permittivities at mutually different frequencies. In this case, the alert generation unit 2 may assess whether the erythrocyte sedimentation rate in the blood sample exceeds the prescribed standard on the basis of a relationship between the plurality of permittivities.

As an indicator of the relationship between the plurality of permittivities, any value calculated from the permittivities may be used to the extent that it indicates a relationship between the plurality of permittivities and allows the erythrocyte sedimentation rate to be estimated. Specific examples of the indicator of the relationship between the plurality of permittivities include the difference, the ratio, and the like. In the case where the difference mentioned above is used for the assessment of the erythrocyte sedimentation rate, the alert generation unit 2 may compare the difference and a prescribed threshold, and may thereby assess whether the erythrocyte sedimentation rate in the blood sample exceeds the prescribed standard.

In the case where permittivity is used for the assessment of the erythrocyte sedimentation rate, the measurement value at a specific time point after the start of measurement or a value based on the measurement value may be used as described above, and also a value obtained from the temporal change in permittivity may be used. That is, the alert generation unit 2 may assess whether the erythrocyte sedimentation rate exceeds the prescribed standard also on the basis of the temporal change in permittivity.

For example, the alert generation unit 2 may calculate the difference between the permittivities obtained at two time points of different measurement times at a specific frequency, and may assess whether the erythrocyte sedimentation rate exceeds the prescribed standard on the basis of the difference. In this case, the erythrocyte sedimentation rate may be assessed as higher than the standard when, for example, the difference between the permittivities at the two time points is not less than a prescribed threshold and furthermore the plus and minus are different between the permittivities at the two time points.

The alert generation unit 2 may assess whether the erythrocyte sedimentation rate exceeds the prescribed standard also on the basis of the increase or decrease in permittivity per certain time. As the indicator of the increase or decrease in permittivity per certain time, any value calculated from the permittivity may be used to the extent that it indicates the increase or decrease in permittivity per unit time and allows the erythrocyte sedimentation rate to be estimated.

The increase or decrease in permittivity per certain time may also be the slope of a tangent line in a graph showing the temporal change in permittivity or a value calculated from the slope, for example. In this case, the alert generation unit 2 may assess whether the erythrocyte sedimentation rate in the blood sample exceeds the prescribed standard on the basis of a relationship between the maximum slope and the minimum slope in the temporal change in permittivity, for example. The relationship between the maximum slope and the minimum slope may be the difference, the ratio, or the like, for example.

In the assessment of the erythrocyte sedimentation rate by the alert generation unit 2 described above, in the case where the measuring unit 1a measures a complex dielectric spectrum, the permittivity used for the assessment may be either the real part or the imaginary part, and is not limited. Whether the alert generation unit 2 assesses the erythrocyte sedimentation rate as higher than the standard when the rate becomes smaller than the threshold or assesses the erythrocyte sedimentation rate as higher than the standard when the rate becomes larger than the threshold may be set in accordance with various conditions as appropriate. Such conditions are, for example, a set frequency, a specific value used for the assessment, whether the permittivity is the real part or the imaginary part, etc.

The measurement of the electrical characteristic of a blood sample and the generation of an alert signal described above can be caused to be performed by the measuring unit 1a and the alert generation unit 2 by creating a program for achieving the function of measuring the electrical characteristic and the function of issuing an alert signal when the erythrocyte sedimentation rate exceeds a prescribed standard, and mounting the program on the measuring unit 1a and the alert generation unit 2 of the electrical characteristic measuring device D1.

In the electrical characteristic measuring device according to the embodiment, in the measurement of the electrical characteristic of a blood sample, an alert signal is issued from the alert generation unit when the erythrocyte sedimentation rate exceeds a prescribed standard. Then, the first alert presentation unit presents an alert on the basis of the signal. Therefore, in the measurement of a blood sample using the electrical characteristic measuring device according to the embodiment, when a blood sample in which the erythrocyte sedimentation rate exceeds the expectation is measured, the user can recognize the erythrocyte sedimentation rate of the blood sample as exceeding the expectation by means of an alert from the first alert presentation unit. As a result, the user can be prevented from falsely recognizing that the measurement result of the electrical characteristic measured in a blood sample in which the erythrocyte sedimentation rate exceeds the expectation is data that are measured in appropriate measurement conditions. Thus, in the electrical characteristic measuring device according to the embodiment, the electrical characteristic of a blood sample can be measured with high accuracy.

2. Modification Embodiment of First Embodiment

Figure 4A:
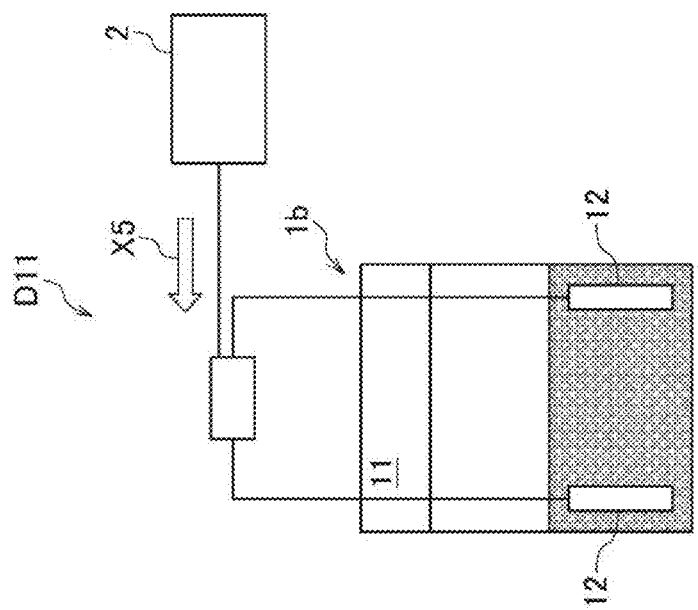
FIGS. 4A and 4B are schematic diagrams showing the operation of an electrical characteristic measuring device according to a modification embodiment of the first embodiment.
Figure 4B:
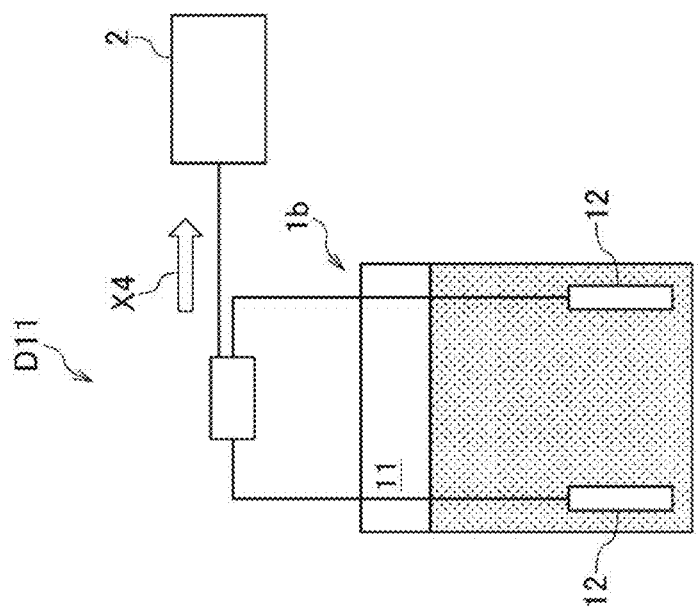

FIGS. 4A and 4B schematically shows the operation of an electrical characteristic measuring device D11 according to a modification embodiment of the first embodiment. The configuration of the electrical characteristic measuring device D11 is the same as the configuration of the electrical characteristic measuring device D1 according to the first embodiment described above except for a measuring unit 1b. Hence, a description of the configuration other than the measuring unit 1b is omitted.

In the electrical characteristic measuring device D11, the measurement of the electrical characteristic of a blood sample by the measuring unit 1b is started. Also in the embodiment, the alert generation unit 2 may acquire measurement values etc. in order to assess the erythrocyte sedimentation rate in the blood sample (arrow X4 of FIG. 4A). When the erythrocyte sedimentation rate in the blood sample exceeds a prescribed standard, the alert generation unit 2 issues an alert signal. The measuring unit 1b stops the measurement of the blood sample in the measuring unit 1b on the basis of the alert signal (FIG. 4B).

In the electrical characteristic measuring device according to the embodiment, the measuring unit stops the measurement of the blood sample on the basis of an alert signal issued from the alert generation unit. In the case where, for example, the electrical characteristics of a plurality of blood samples are measured, the measurement of a blood sample in which it is difficult to measure the electrical characteristic in an appropriate state may be stopped, and thereby the measurement of the next blood sample can be started. Therefore, in the electrical characteristic measuring device according to the embodiment, a plurality of blood samples can be measured more efficiently. Otherwise, the configuration and the effect thereof are similar to those of the electrical characteristic measuring device according to the first embodiment described above.

3. Second Embodiment

Figure 5:
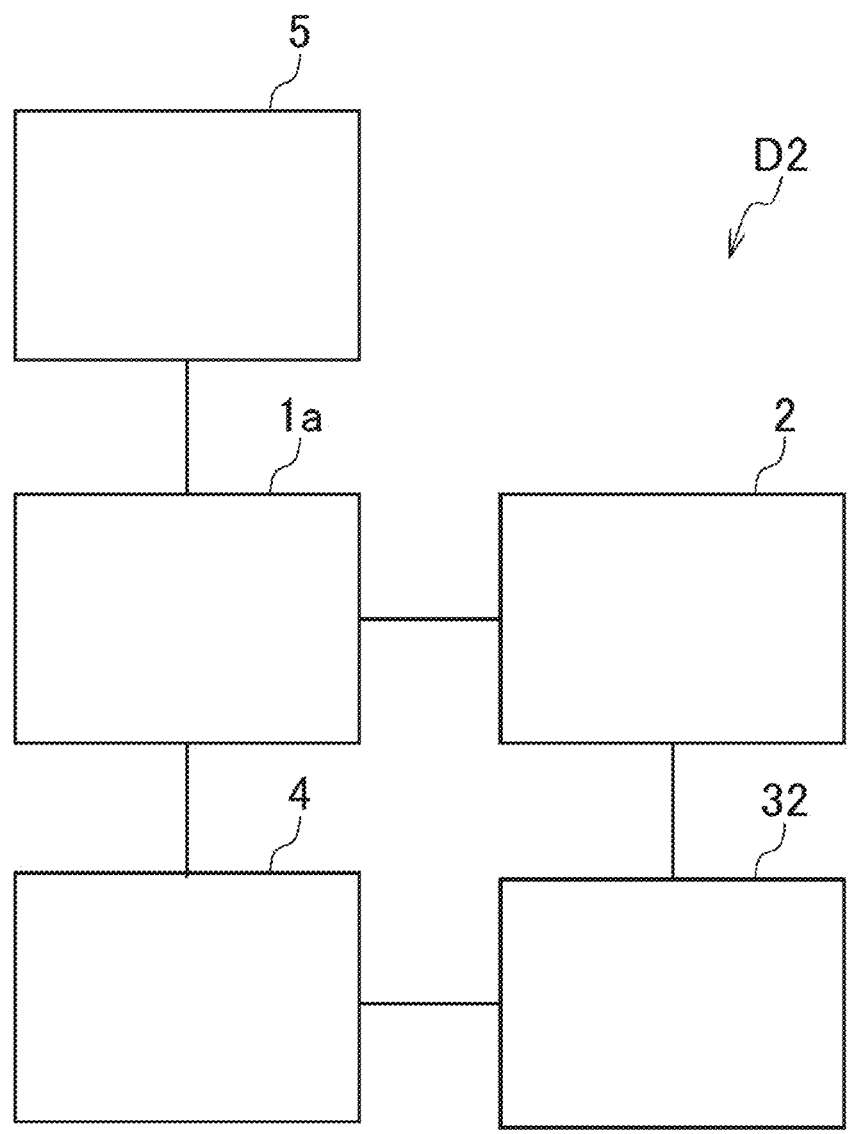
FIG. 5 is a schematic diagram showing the configuration of an electrical characteristic measuring device according to a second embodiment of the present disclosure.

FIG. 5 schematically shows the configuration of an electrical characteristic measuring device according to a second embodiment of the present disclosure. In the drawing, the electrical characteristic measuring device indicated by reference character D2 includes a second alert presentation unit 32. The same configuration as the electrical characteristic measuring device D1 according to the first embodiment described above is marked with the same reference character, and a description thereof is omitted.

<Second Alert Presentation Unit>

The second alert presentation unit 32 presents, for data obtained by measuring the electrical characteristic, the presence or absence of an alert signal generated during measurement. The second alert presentation unit 32 can present the presence or absence of an alert signal generated during the measurement of the electrical characteristic by, for example, creating a log when the alert generation unit 2 issues an alert signal and referring to the log.

The configuration of the second alert presentation unit 32 is not particularly limited to the extent that it can present the presence or absence of an alert signal to the user. For example, a display, a printer, a lighting device, a loudspeaker, etc. may be employed for the second alert presentation unit 32.

Figure 6A:
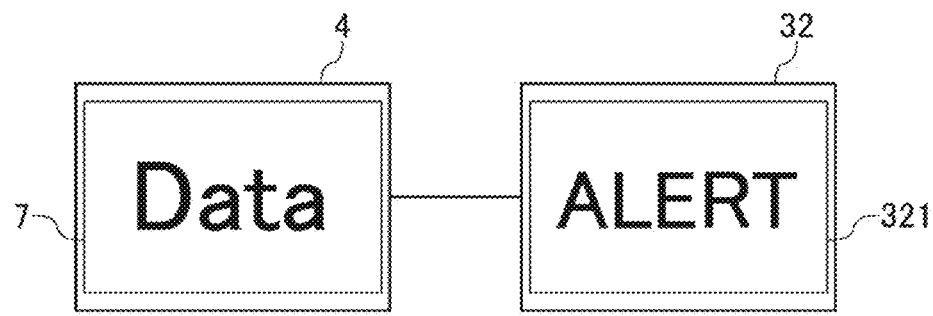
FIGS. 6A to 6C are schematic diagrams showing an example of the presentation of an alert in a second alert presentation unit.
Figure 6B:
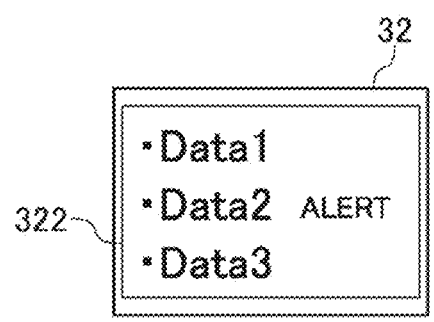

In the case where a display is employed for the second alert presentation unit 32, when, for example, an alert signal was issued from the alert generation unit 2 during the measurement of data 7, the second alert presentation unit 32 may display an alert 321 or the like when the data 7 are displayed on the display unit 4, and may thereby present the presence or absence of an alert signal issued during measurement (FIG. 6A). Further, for example, the second alert presentation unit 32 may display a list 322 of pieces of data, and may show the presence or absence of generation of an alert signal for each piece of data (FIG. 6B).

Figure 6C:
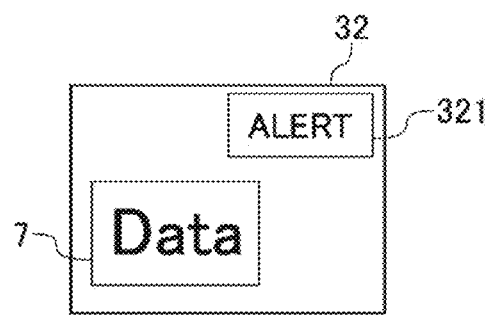

Further, in the case where the display unit 4 and the second alert presentation unit 32 are configured using one display and data 7 are seen, when an alert signal is issued during the measurement of a blood test sample in which the data are acquired, an alert 321 may be displayed on a part of the screen, and thus the presence or absence of generation of an alert signal by the alert generation unit 2 may be presented (FIG. 6C). Further, in the case where, for example, a plurality of pieces of data 7 are seen simultaneously on the display mentioned above, a configuration in which, for a piece of data 7 for which an alert signal is issued during measurement, an alert 321 is displayed along with the piece of data 7 is possible.

The second alert presentation unit 32 may also be provided in the electrical characteristic measuring device together with the first alert presentation unit 31 described above. That is, the second alert presentation unit 32 may be provided in the electrical characteristic measuring device D1 according to the first embodiment or the electrical characteristic measuring device D11 according to the modification embodiment of the first embodiment described above.

In the electrical characteristic measuring device according to the embodiment, since the second alert presentation unit is included, the user can, after the measurement of the electrical characteristic of a blood sample, check the presence or absence of an alert signal issued during the measurement of the data obtained. Thus, the user can be prevented from falsely recognizing that the measurement result of the electrical characteristic measured in a blood sample in which the erythrocyte sedimentation rate exceeds the expectation is data that are measured in appropriate measurement conditions, and the measurement of the electrical characteristic of a blood sample can be performed with high accuracy.

Furthermore, the user can check the presence or absence of an alert signal even after the measurement of the blood sample, and can therefore distinguish between data measured in appropriate measurement conditions and data measured in inappropriate measurement conditions more reliably. Otherwise, the configuration and the effect thereof are similar to those of the electrical characteristic measuring device D1 according to the first embodiment described above.

The effects described above are only examples and the effect is not limited to them, and there may be other effects.

Additionally, the present technology may also be configured as below.

(1)

An electrical characteristic measuring device including:

a measuring unit configured to measure an electrical characteristic of a blood sample; and an alert generation unit configured to issue an alert signal when an erythrocyte sedimentation rate in the blood sample exceeds a prescribed standard during measurement of the blood sample.

(2)

The electrical characteristic measuring device according to (1), wherein the alert generation unit assesses whether the erythrocyte sedimentation rate exceeds a prescribed standard on the basis of an electrical characteristic obtained by measuring the blood sample.

(3)

The electrical characteristic measuring device according to (2), wherein the alert generation unit uses one or more permittivities at a specific frequency as the electrical characteristic.

(4)

The electrical characteristic measuring device according to (3), wherein the alert generation unit uses, as the permittivity, a permittivity measured at a specific time point after a start of measurement of the blood sample.

(5)

The electrical characteristic measuring device according to (4), wherein the alert generation unit uses, as the permittivity, a plurality of permittivities at mutually different frequencies and assesses whether the erythrocyte sedimentation rate exceeds a prescribed standard on the basis of a relationship between the plurality of permittivities.

(6)

The electrical characteristic measuring device according to (3), wherein the alert generation unit assesses whether the erythrocyte sedimentation rate exceeds a prescribed standard on the basis of a temporal change in the permittivity.

(7)

The electrical characteristic measuring device according to (6), wherein the alert generation unit assesses whether the erythrocyte sedimentation rate exceeds a prescribed standard on the basis of an increase or decrease in the permittivity per certain time.

(8)

The electrical characteristic measuring device according to any one of (1) to (7), wherein the measuring unit includes at least a pair of electrodes in a position in contact with the blood sample.

(9)

The electrical characteristic measuring device according to (8), wherein the pair of electrodes are arranged facing each other, and surfaces of the electrodes facing each other are disposed along a direction in which red blood cells in the blood sample sediment.

(10)

The electrical characteristic measuring device according to any one of (1) to (9), including a first alert presentation unit configured to present an alert during measurement of the blood sample on the basis of the alert signal.

(11)

The electrical characteristic measuring device according to any one of (1) to (10), wherein the measuring unit stops measurement of the blood sample on the basis of the alert signal.

(12)

The electrical characteristic measuring device according to any one of (1) to (11), including a second alert presentation unit configured to present, for data obtained by measuring the electrical characteristic, presence or absence of the alert signal generated during measurement.

(13)

A program for causing a computer to execute:

a measurement function of measuring an electrical characteristic of a blood sample; and an alert generation function of issuing an alert signal when an erythrocyte sedimentation rate in the blood sample exceeds a prescribed standard during measurement of the blood sample.

EXAMPLES

1. Experiment Example 1

In this Experiment Example, it was verified whether the electrical characteristic obtained by measuring a blood test samples exhibits a change that is peculiar to a blood test sample having a high erythrocyte sedimentation rate.
<Material and Method>
This Experiment Example used a blood sample in which the erythrocyte sedimentation rate was assessed as higher than that of an able-bodied person in advance, a normal blood sample, and a blood sample in which the fibrinolytic system was enhanced. For the blood sample in which the fibrinolytic system was enhanced, a tissue plasminogen activator that promotes the fibrinolytic system was added, and thereby a blood sample in which the fibrinolytic system was artificially enhanced was adjusted.

Figure 7B:
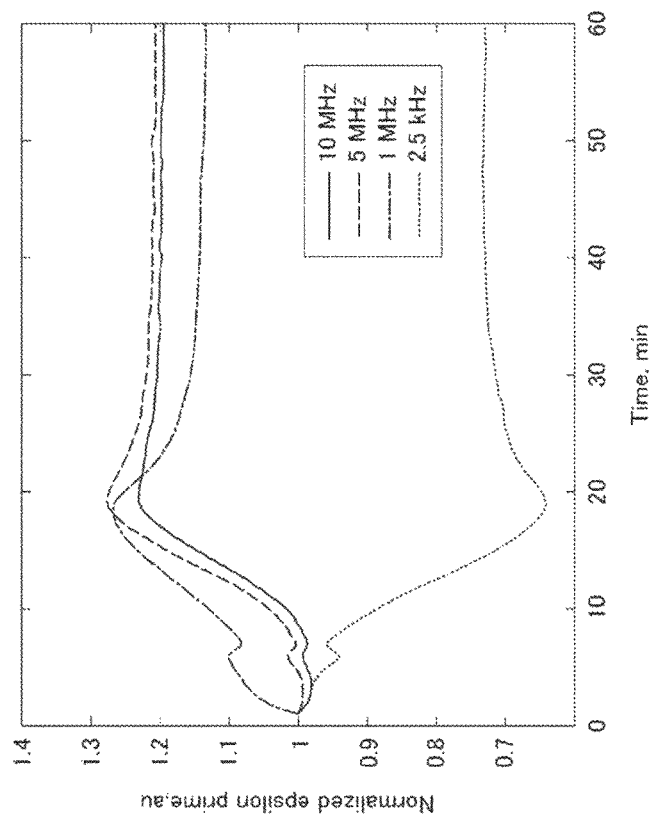
FIG. 7B is a drawing-substitute graph showing the temporal change in permittivity at each frequency out of the dielectric spectrum shown in FIG. 7A.
Figure 7A:
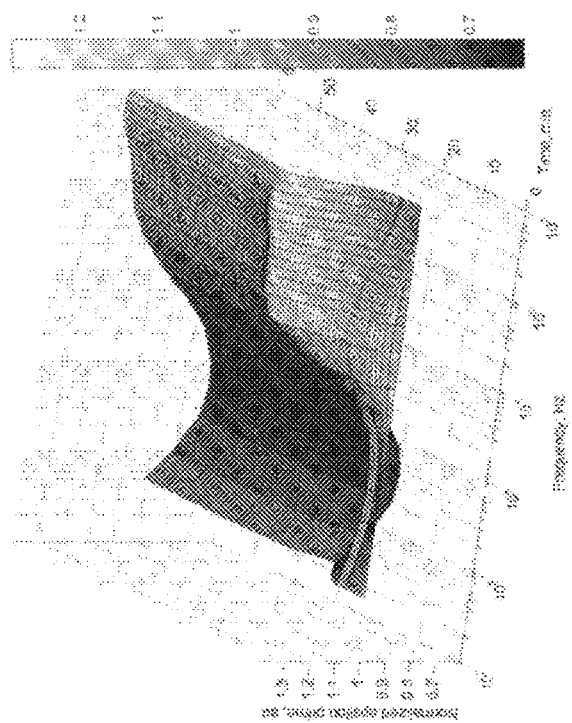
FIG. 7A is a drawing-substitute graph showing a dielectric spectrum of a blood sample derived from an able-bodied person measured in Experiment Example 1.
Figure 8A:
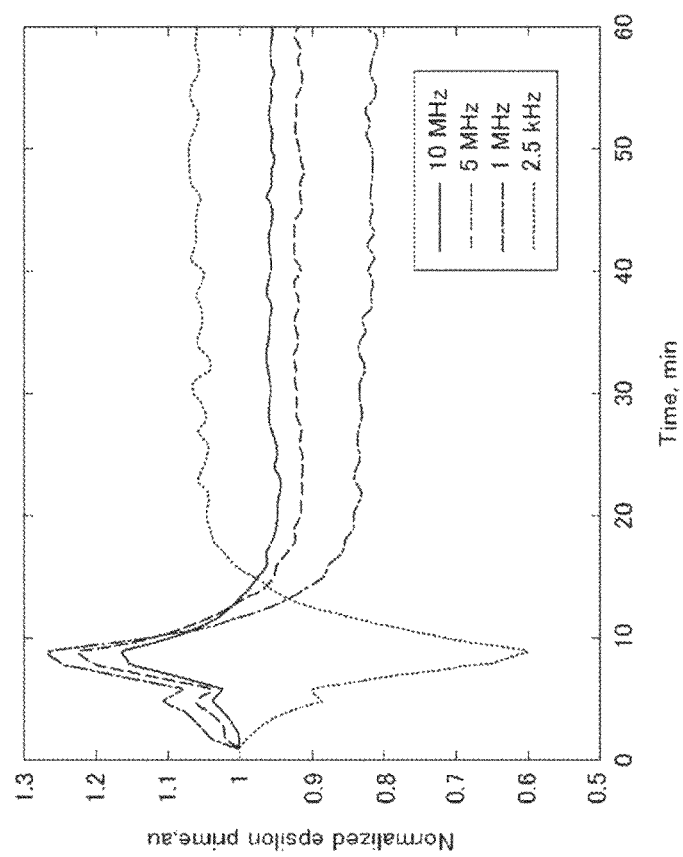
FIG. 8A is a drawing-substitute graph showing a dielectric spectrum of a blood sample measured in Experiment Example 1 that has an erythrocyte sedimentation rate higher than that of an able-bodied person.
Figure 8B:
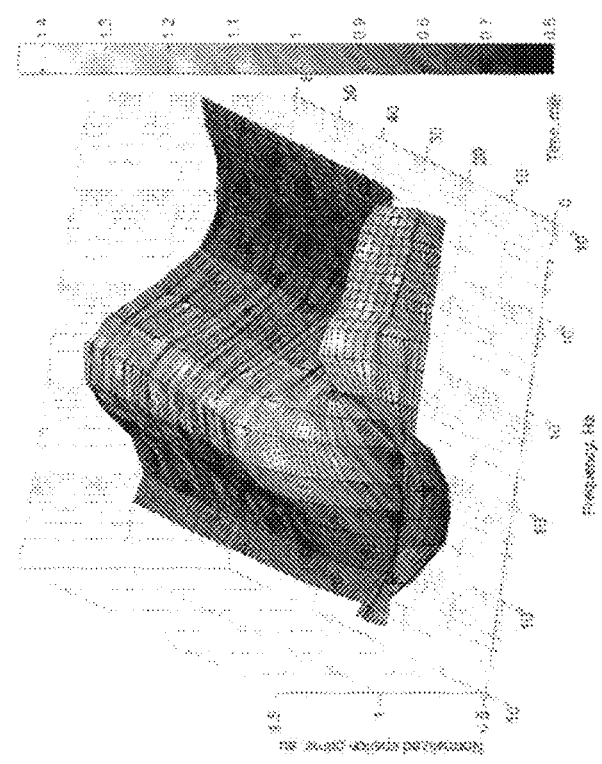
FIG. 8B is a drawing-substitute graph showing the temporal change in permittivity at each frequency out of the dielectric spectrum shown in FIG. 8A.
Figure 9B:
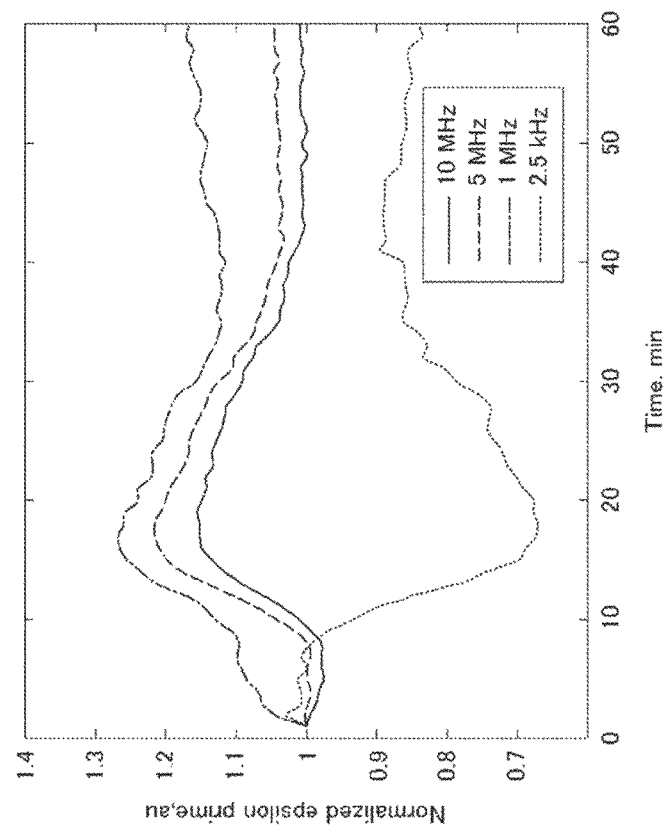
FIG. 9B is a drawing-substitute graph showing the temporal change in permittivity at each frequency out of the dielectric spectrum shown in FIG. 9A.
Figure 9A:
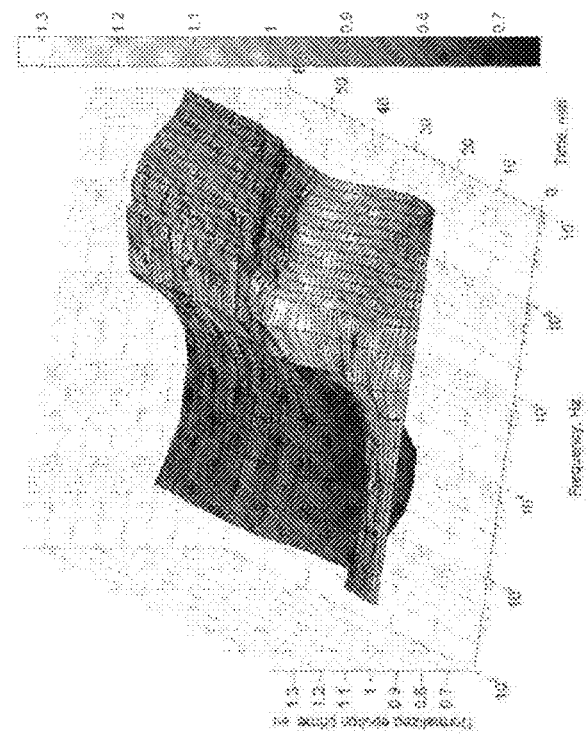
FIG. 9A is a drawing-substitute graph showing a dielectric spectrum of a blood sample measured in Experiment Example 1 in which the fibrinolytic system is enhanced.

Each blood sample was collected from a vein, and was then collected to a vacuum blood collection tube provided with sodium citrate, which is an anticoagulant, in advance. After that, a prescribed amount of a calcium chloride aqueous solution was added to each blood test sample to resume the blood coagulation reaction in the blood sample, and a dielectric spectrum of each blood sample was measured. The measurement temperature was set to 37° C.
<Results>
The results of this Experiment Example are shown in FIGS. 7A and 7B to FIGS. 9A and 9B. FIG. 7A shows a dielectric spectrum of the blood sample derived from an able-bodied person, and FIG. 7B shows the temporal change in permittivity at each frequency out of the dielectric spectrum shown in FIG. 7A. FIG. 8A shows a dielectric spectrum of the blood sample having an erythrocyte sedimentation rate higher than that of an able-bodied person, and FIG. 8B shows the temporal change in permittivity at each frequency out of the dielectric spectrum shown in FIG. 8A. FIG. 9A shows a dielectric spectrum of the blood sample in which the fibrinolytic system is enhanced, and FIG. 9B shows the temporal change in permittivity at each frequency out of the dielectric spectrum shown in FIG. 9A.

From the results of this Experiment Example, it has been found that the dielectric spectrum of the blood sample having an erythrocyte sedimentation rate higher than that of an able-bodied person has a distinctive difference from the dielectric spectrum of an able-bodied person. Further, it has been found that the dielectric spectrum of the blood sample having an erythrocyte sedimentation rate higher than that of an able-bodied person has a distinctive change also as compared to the dielectric spectrum of the blood sample in which the fibrinolytic system is enhanced. Therefore, it has been verified that the erythrocyte sedimentation rate of a blood sample can be estimated on the basis of a dielectric spectrum.

2. Experiment Example 2

In this Experiment Example, it was verified whether a blood sample having an erythrocyte sedimentation rate higher than that of an able-bodied person can be identified on the basis of the permittivity.

Figure 10A:
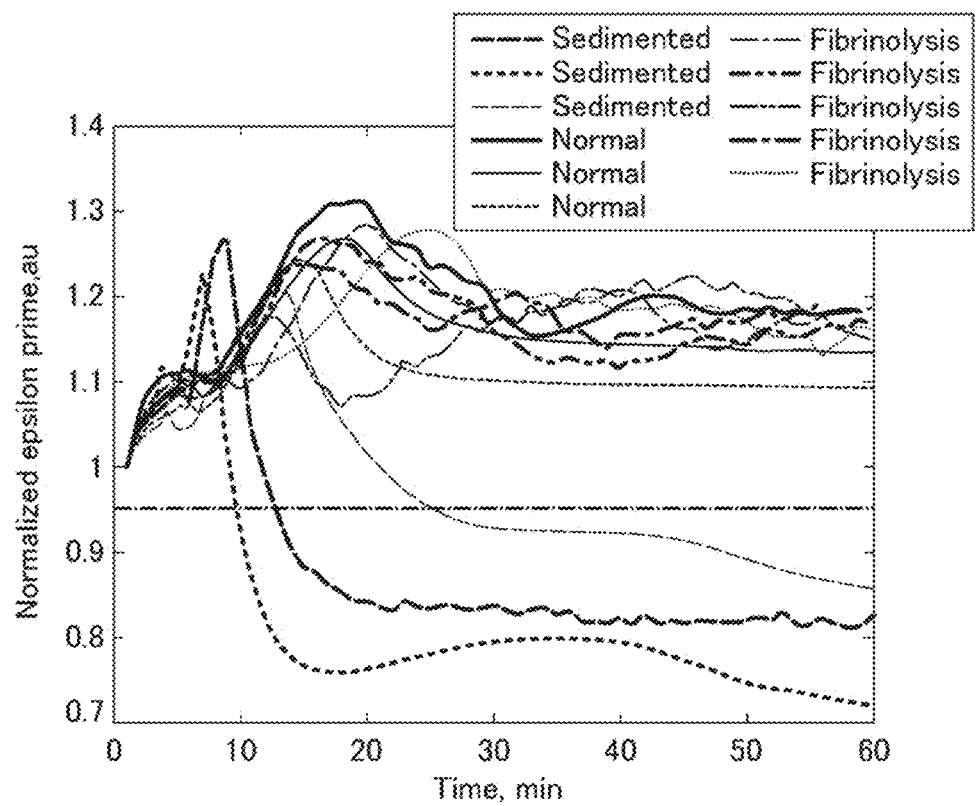
FIGS. 10A and 10B are drawing-substitute graphs showing the results of Experiment Example 2.
Figure 10B:
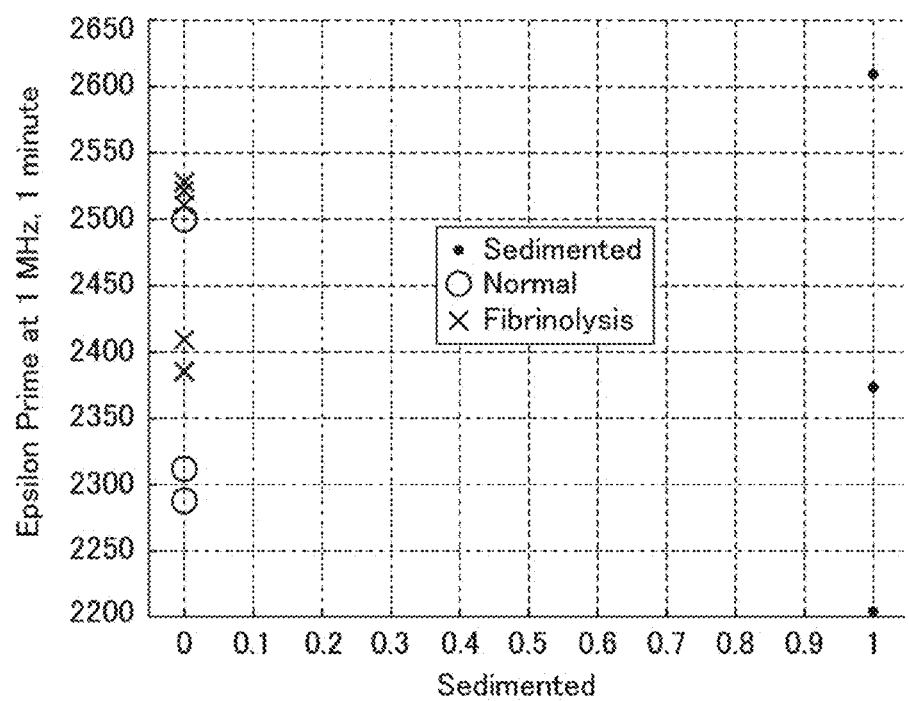

<Material and Method>
This Experiment Example used 3 blood test samples derived from an able-bodied person, 3 blood test samples having an erythrocyte sedimentation rate higher than that of an able-bodied person, and 5 blood test samples in which the fibrinolytic system was enhanced. The measurement of a dielectric spectrum was performed in a similar manner to Experiment Example 1 described above.
<Results>
The results of this Experiment Example are shown in FIGS. 10A and 10B. The vertical axis of FIG. 10A represents a normalized permittivity at 1 MHz, and the horizontal axis represents the time elapsed from the start of measurement (minutes). The normalization was performed on the basis of the measurement value 1 minute after the resumption of the blood coagulation reaction, which was based on the addition of a calcium chloride aqueous solution into the blood sample.

The vertical axis of FIG. 10B represents the permittivity at 1 MHz 1 minute after the start of measurement. The horizontal axis of FIG. 10B represents the flag of whether the erythrocyte sedimentation rate exceeds a prescribed standard, shown by 2 values in which the sample in which the rate exceeded the standard is classified as "1" and the sample in which the rate did not reach the standard is classified as "0".

As shown in FIG. 10A, in the blood samples having an erythrocyte sedimentation rate higher than that of an able-bodied person ("Sedimented" in FIG. 10A), the normalized permittivity became less than 0.95 during measurement. As shown in FIG. 10B, the blood test samples have been able to be categorized into 2 groups of samples having an erythrocyte sedimentation rate higher than that of an able-bodied person and the other samples by using "0.95" as a threshold and marking "1" on the blood test sample in which the normalized permittivity became less than 0.95.

As shown in FIG. 10A, in each of the blood samples derived from an able-bodied person ("Normal" in FIG. 10A) and the blood samples in which the fibrinolytic system was enhanced ("Fibrinolysis" in FIG. 10A), the normalized permittivity did not fall below "1" during the 60 minutes from the start to the end of measurement. Therefore, the threshold is not limited to 0.95, and a result similar to the assessment result shown in FIG. 10B can be obtained when the threshold is set to any value between 0.95 and 1.

From the results of this Experiment Example, it has been revealed that, by providing a threshold to the permittivity or the normalized permittivity, the blood sample having an erythrocyte sedimentation rate higher than that of an able-bodied person can be distinguished from the blood sample derived from an able-bodied person and the blood sample in which the fibrinolytic system is enhanced. That is, it has been shown that whether the sample in question is a blood sample in which red blood cells sediment faster than the previously expected erythrocyte sedimentation rate can be assessed by comparing the permittivity or a value obtained on the basis of the permittivity and a threshold.

3. Experiment Example 3

In this Experiment Example, like in Experiment Example 2, it was verified whether a blood sample having an erythrocyte sedimentation rate higher than that of an able-bodied person can be identified on the basis of the permittivity.
<Material and Method>
This Experiment Example was performed in a similar manner to Experiment Example 2.

<Results>

Figure 11A:
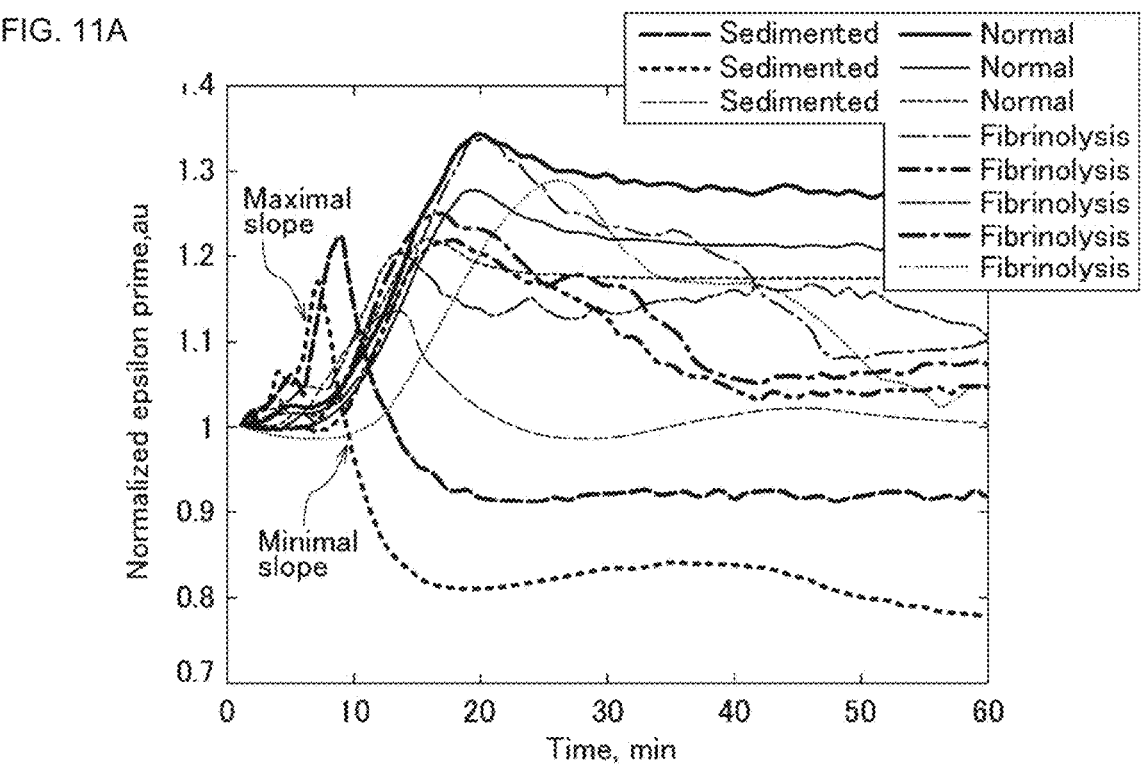
FIGS. 11A and 11B are drawing-substitute graphs showing the results of Experiment Example 3.
Figure 11B:
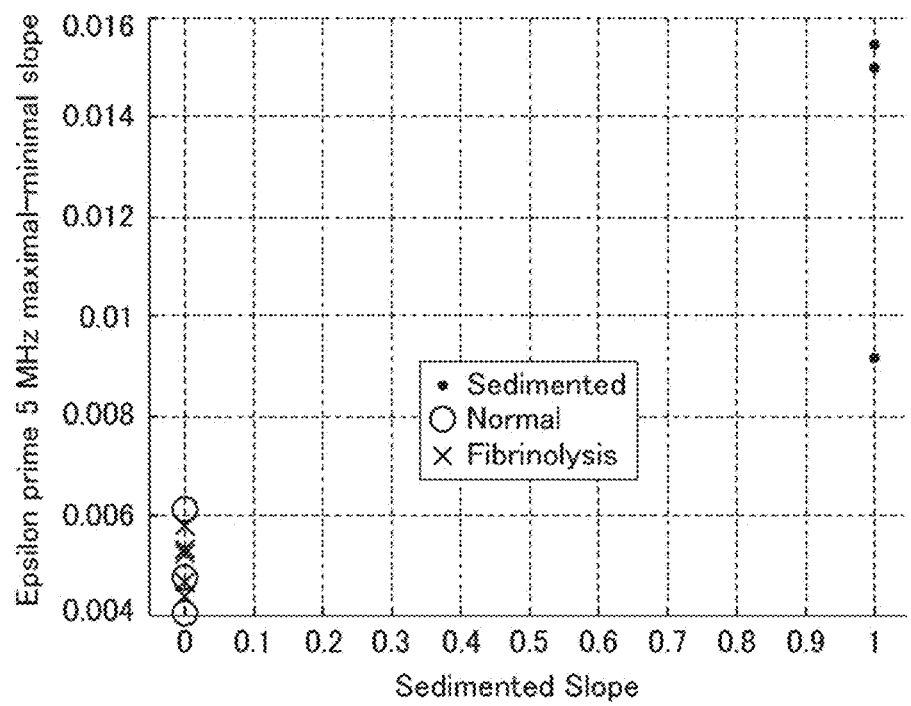

The results of this Experiment Example are shown in FIGS. 11A and 11B. The vertical axis of FIG. 11A represents a normalized permittivity at 5 MHz, and the horizontal axis represents the time elapsed from the start of measurement (minutes). Like in Experiment Example 2, the normalization was performed on the basis of the measurement value 1 minute after the resumption of the blood coagulation reaction, which was based on the addition of a calcium chloride aqueous solution into the blood sample.

The vertical axis of FIG. 11B represents the difference between the maximum slope and the minimum slope in the permittivity (5 MHz) during the 1 minute from the start of measurement, and the horizontal axis represents the flag of whether the erythrocyte sedimentation rate exceeds a prescribed standard, shown by 2 values in which the sample in which the rate exceeded the standard is classified as "1" and the sample in which the rate did not reach the standard is classified as "0".

As shown in FIG. 11B, in the blood samples having an erythrocyte sedimentation rate higher than that of an able-bodied person ("Sedimented" in FIG. 11B), the difference between the maximum slope and the minimum slope in the normalized permittivity was larger than 0.007. By using "0.007" as a threshold and marking "1" on the blood test sample in which the difference mentioned above exceeded 0.007, the blood test samples have been able to be categorized into 2 groups of samples having an erythrocyte sedimentation rate higher than that of an able-bodied person and the other samples.

As shown in FIG. 11B, the difference between the maximum slope and the minimum slope did not exceed "0.007" in any of the blood samples derived from an able-bodied person ("Normal" in FIG. 11B) and the blood samples in which the fibrinolytic system was enhanced ("Fibrinolysis" in FIG. 11B), and the difference mentioned above exceeded "0.008" in the blood samples having an erythrocyte sedimentation rate higher than that of an able-bodied person. Therefore, the threshold is not limited to 0.007, and a result similar to the assessment result shown in FIG. 11B can be obtained when the threshold is set to any value between 0.007 and 0.008.

From the results of this Experiment Example, it has been revealed that, by providing a threshold to the difference between the maximum slope and the minimum slope in the temporal change in the permittivity or the normalized permittivity, the blood sample having an erythrocyte sedimentation rate higher than that of an able-bodied person can be distinguished from the blood sample derived from an able-bodied person and the blood sample in which the fibrinolytic system is enhanced. That is, it has been shown that whether the sample in question is a blood sample in which red blood cells sediment faster than the previously expected erythrocyte sedimentation rate can be assessed by comparing the permittivity or a value obtained on the basis of the permittivity and a threshold.

4. Experiment Example 4

In this Experiment Example, like in Experiment Examples 2 and 3, it was verified whether a blood sample having an erythrocyte sedimentation rate higher than that of an able-bodied person can be identified on the basis of the permittivity.

<Material and Method>

This Experiment Example was performed in a similar manner to Experiment Example 2.

<Results>

Figure 12A:
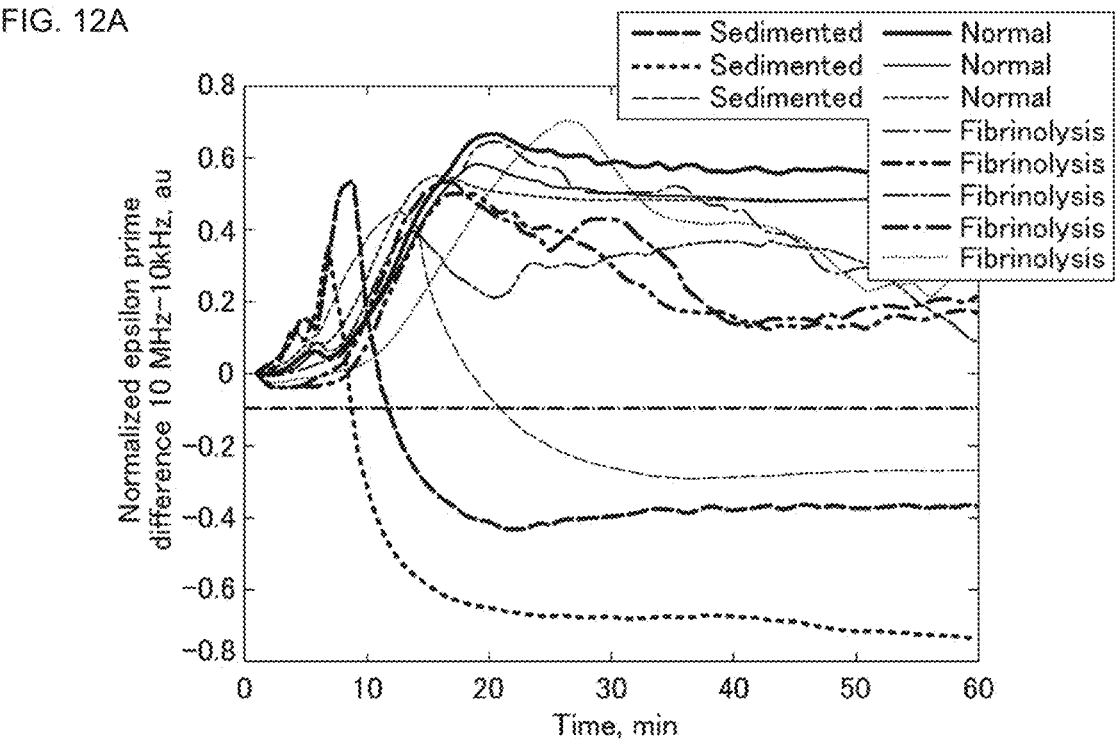
FIGS. 12A and 12B are drawing-substitute graphs showing the results of Experiment Example 4.
Figure 12B:
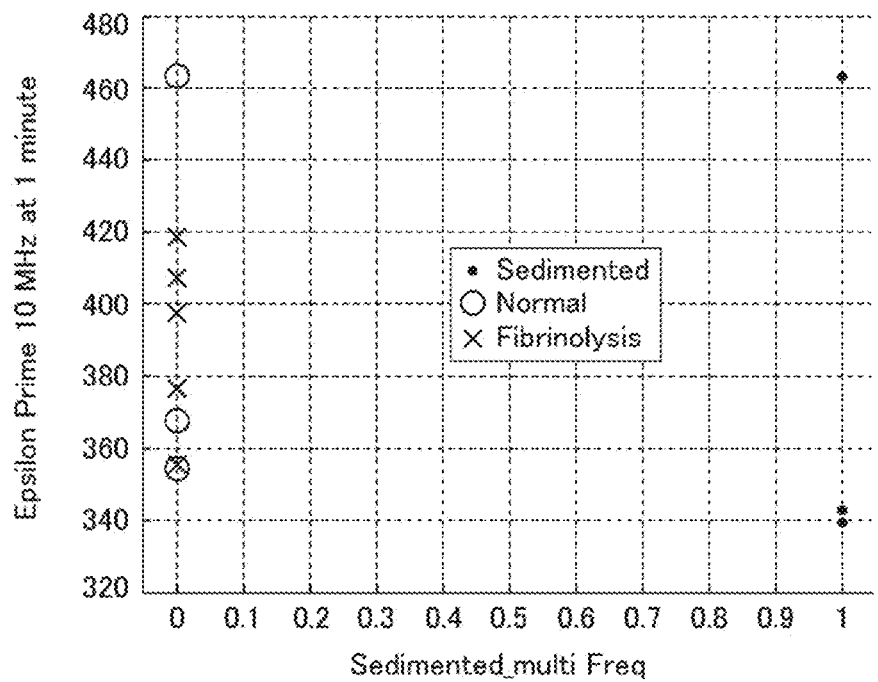

The results of this Experiment Example are shown in FIGS. 12A and 12B. The vertical axis of FIG. 12A represents the difference between a normalized permittivity at 10 MHz and a normalized permittivity at 10 kHz, and the horizontal axis represents the time elapsed from the start of measurement (minutes). Like in Experiment Example 2, the normalization was performed on the basis of the measurement value 1 minute after the resumption of the blood coagulation reaction, which was based on the addition of a calcium chloride aqueous solution into the blood sample.

The vertical axis of FIG. 12B represents the permittivity at 10 MHz 1 minute after the start of measurement, and the horizontal axis represents the flag of whether the erythrocyte sedimentation rate exceeds a prescribed standard, shown by 2 values in which the sample in which the rate exceeded the standard is classified as "1" and the sample in which the rate did not reach the standard is classified as "0".

As shown in FIG. 12A, in the blood samples having an erythrocyte sedimentation rate higher than that of an able-bodied person ("Sedimented" in FIG. 12A), the difference between the normalized permittivity at 10 MHz and the normalized permittivity at 10 kHz became smaller than −0.1. As shown in FIG. 12B, by marking "1" on the blood test sample in which the difference mentioned above became smaller than −0.1, the blood test samples have been able to be categorized into 2 groups of samples having an erythrocyte sedimentation rate higher than that of an able-bodied person and the other samples.

From the results of this Experiment Example, it has been revealed that, by calculating the difference between the permittivities or the normalized frequencies at a certain frequency and another frequency and providing a threshold to the difference mentioned above, the blood sample having an erythrocyte sedimentation rate higher than that of an able-bodied person can be distinguished from the blood sample derived from an able-bodied person ("Normal" in FIG. 12B) and the blood sample in which the fibrinolytic system is enhanced ("Fibrinolysis" in FIG. 12B).

That is, it has been shown that whether the sample in question is a blood sample in which red blood cells sediment faster than the previously expected erythrocyte sedimentation rate can be assessed by comparing the permittivity or a value obtained on the basis of the permittivity and a threshold.

5. Experiment Example 5

In this Experiment Example, it was verified whether a blood sample having an erythrocyte sedimentation rate higher than that of an able-bodied person can be identified on the basis of a dielectric spectrum, especially even by the imaginary part of a complex dielectric spectrum.

<Material and Method>

This Experiment Example used 1 blood test sample derived from an able-bodied person, 1 blood test sample having an erythrocyte sedimentation rate higher than that of an able-bodied person, and 3 blood test samples in which the fibrinolytic system was enhanced. The measurement of a dielectric spectrum was performed in a similar manner to Experiment Example 1 described above.

<Results>

Figure 13A:
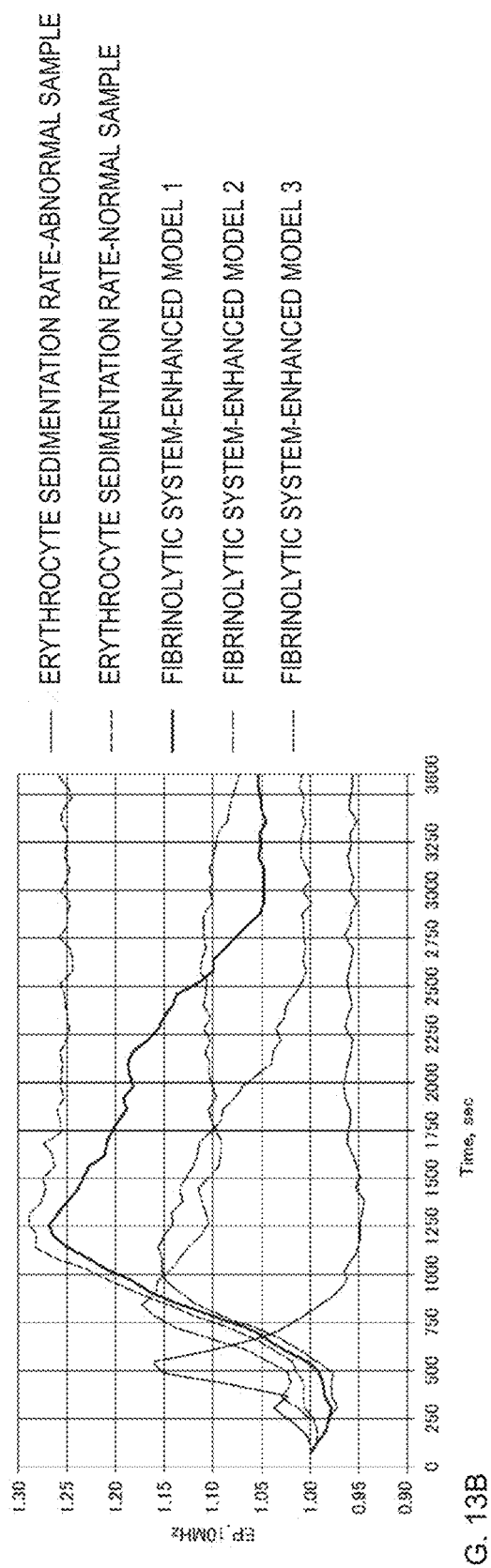
FIGS. 13A and 13B are drawing-substitute graphs showing the temporal change in complex permittivity at 10 MHz measured in Experiment Example 5.
Figure 13B:
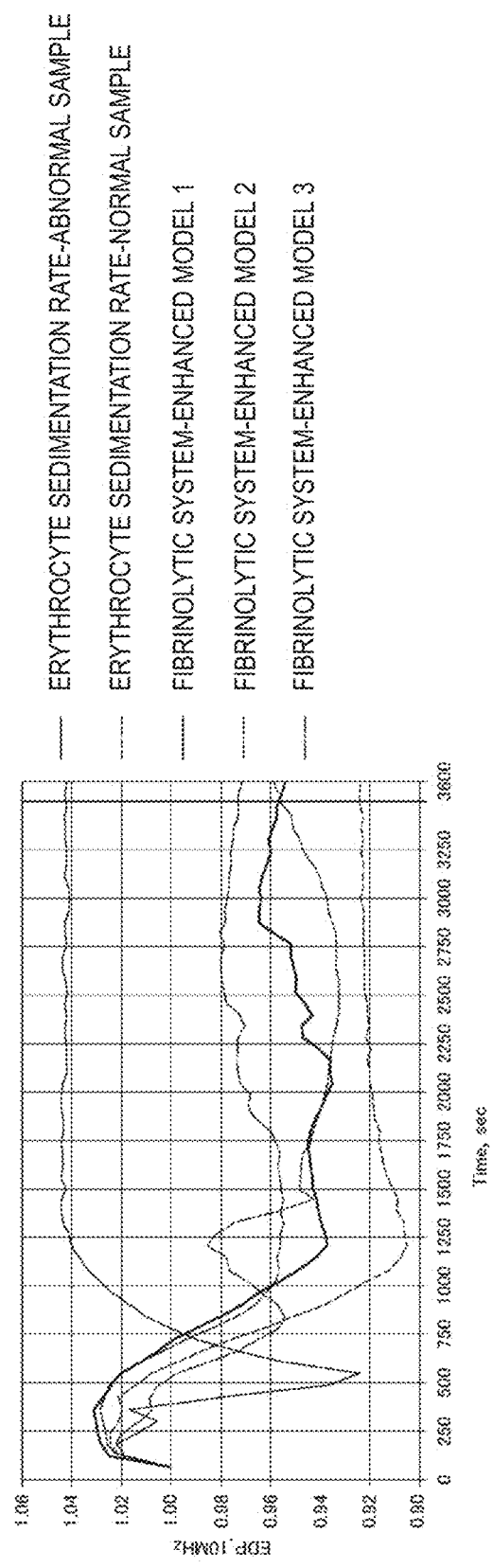

The results of this Experiment Example are shown in FIGS. 13A and 13B. The vertical axis of FIG. 13A represents the permittivity of the real part at 10 MHz, and the horizontal axis represents the time elapsed from the start of measurement. On the other hand, the vertical axis of FIG.

13B represents the permittivity of the imaginary part at 10 MHz, and the horizontal axis represents the time elapsed from the start of measurement.

As shown in FIG. 13A and FIG. 13B, for the permittivity in the blood sample derived from an able-bodied person, a curve like one in which the permittivity increased or decreased with the lapse of time from the start of measurement and upon reaching a peak gently increased or decreased was obtained. On the other hand, the permittivity in the blood sample having an erythrocyte sedimentation rate higher than that of an able-bodied person ("Erythrocyte sedimentation rate-abnormal sample") quickly changed direction in the course of increase or decrease so as to reverse the plus and minus. In the blood samples in which the fibrinolytic system is enhanced, when the blood coagulation reaction proceeds to some degree, the fibrinolytic system begins to work and the coagulated blood is dissolved again. Accordingly, also for the permittivity, a curve in which the permittivity changed direction in the course of increase or decrease so as to reverse the plus and minus was obtained. However, this change was gentler than the change in the blood test sample having a high erythrocyte sedimentation rate.

From the results of this Experiment Example, it has been found that the dielectric spectrum of the blood sample having an erythrocyte sedimentation rate higher than that of an able-bodied person has a distinctive change not only in the real part but also in the imaginary part as compared to the dielectric spectrum of an able-bodied person. Further, in regard to the imaginary part, it has been found that the temporal change in permittivity in the blood sample having an erythrocyte sedimentation rate higher than that of an able-bodied person has a distinctive change also as compared to the dielectric spectrum of the blood sample in which the fibrinolytic system is enhanced. Thus, it has been verified that the erythrocyte sedimentation rate of a blood sample can be estimated on the basis of a dielectric spectrum in both the real part and the imaginary part.

REFERENCE SIGNS LIST

D1, D11, D2 electrical characteristic measuring device
S1, S2 facing surface
1a, 1b measuring unit
11 sample storage space
12 electrode
2 alert generation unit
31 first alert presentation unit
32 second alert presentation unit
321 alert
322 list
4 display unit
5 memory unit
6 application unit
7 data

The invention claimed is:

1. An electrical characteristic measuring device, comprising:
an analyzer comprising:
a first electrode; and
a second electrode, wherein
the first electrode and the second electrode are configured to measure an electrical characteristic of each blood sample of a plurality of blood samples,
a first surface of the first electrode faces a second surface of the second electrode, and
the first surface and the second surface extend in a first direction parallel to a second direction of sedimentation of each blood sample; and
a central processing unit (CPU) configured to:
acquire a set of measurement values for each blood sample of the plurality of blood samples from the first electrode and the second electrode;
determine an erythrocyte sedimentation rate of each blood sample of the plurality of blood samples based on the set of measurement values corresponding to each blood sample of the plurality of blood samples;
compare the erythrocyte sedimentation rate of each blood sample of the plurality of blood samples with a threshold value;
determine at least one blood sample of the plurality of blood samples based on the comparison;
use at least one permittivity at a specific frequency as the electrical characteristic of the at least one blood sample;
determine that the erythrocyte sedimentation rate of the at least one blood sample is greater than the threshold value based on a temporal change in the at least one permittivity and based on one of an increase or a decrease in the at least one permittivity per unit time;
generate an alert message based on the determination that the erythrocyte sedimentation rate of the at least one blood sample is greater than the threshold value; and
control a display screen to concurrently display the alert message and the set of measurement values corresponding to the at least one blood sample.

2. The electrical characteristic measuring device according to claim 1, wherein the CPU is further configured to use, as the at least one permittivity, a permittivity at a specific time point after a start of the measurement of the electrical characteristic of the at least one blood sample.

3. The electrical characteristic measuring device according to claim 1,
wherein the CPU is further configured to:
use, as the at least one permittivity, a plurality of permittivities at mutually different frequencies; and
determine that the erythrocyte sedimentation rate of the at least one blood sample is greater than the threshold value based on a relationship between the plurality of permittivities.

4. The electrical characteristic measuring device according to claim 1, wherein the first electrode and the second electrode are in contact with the at least one blood sample.

5. The electrical characteristic measuring device according to claim 1, wherein the analyzer is further configured to stop the measurement of the electrical characteristic of each blood sample of the plurality of blood samples based on the alert message.

6. The electrical characteristic measuring device according to claim 1, wherein the CPU is further configured to control the display screen to display information that indicates presence or absence of the alert message.

7. A non-transitory computer-readable medium having stored thereon computer-executable instructions that, when executed by a computer, cause the computer to execute operations, the operations comprising:
measuring, via a first electrode and a second electrode of an analyzer, an electrical characteristic of each blood sample of a plurality of blood samples, wherein
a first surface of the first electrode faces a second surface of the second electrode, and the first surface and the second surface extend in a first direction parallel to a second direction of sedimentation of each blood sample;

acquiring a set of measurement values for each blood sample of the plurality of blood samples from the first electrode and the second electrode;

determining an erythrocyte sedimentation rate of each blood sample of the plurality of blood samples based on the set of measurement values corresponding to each blood sample of the plurality of blood samples;

comparing the erythrocyte sedimentation rate of each blood sample of the plurality of blood samples with a threshold value;

determining at least one blood sample of the plurality of blood samples based on the comparison;

using at least one permittivity at a specific frequency as the electrical characteristic of the at least one blood sample;

determining that the erythrocyte sedimentation rate of the at least one blood sample is greater than the threshold value based on a temporal change in the at least one permittivity and based on one of an increase or a decrease in the at least one permittivity per unit time;

generating an alert message based on the determination that the erythrocyte sedimentation rate of the at least one blood sample is greater than the threshold value; and controlling a display screen to concurrently display the alert message and the set of measurement values corresponding to the at least one blood sample.

* * * * *